(12) United States Patent
Ryu et al.

(10) Patent No.: US 12,049,444 B2
(45) Date of Patent: Jul. 30, 2024

(54) MONOMETHYL FUMARATE PRECURSOR DRUG COMPOUNDS AND PHARMACEUTICAL COMPOSITIONS THEREOF

(71) Applicant: AGATHONBIO CO., LTD., Chungcheongbuk-do (KR)

(72) Inventors: Hyung-Chul Ryu, Gyeonggi-do (KR); Jae-Sun Kim, Gyeonggi-do (KR); Jee-Woong Lim, Gyeonggi-do (KR); Yeon-Woo Son, Gyeonggi-do (KR)

(73) Assignee: AGATHONBIO CO., LTD., Chungcheongbuk-do (KR)

( * ) Notice: Subject to any disclaimer, the term of this patent is extended or adjusted under 35 U.S.C. 154(b) by 583 days.

(21) Appl. No.: 17/426,287

(22) PCT Filed: Jan. 29, 2020

(86) PCT No.: PCT/KR2020/001368
§ 371 (c)(1),
(2) Date: Jul. 28, 2021

(87) PCT Pub. No.: WO2020/159228
PCT Pub. Date: Aug. 6, 2020

(65) Prior Publication Data
US 2021/0387939 A1    Dec. 16, 2021

(30) Foreign Application Priority Data
Jan. 30, 2019    (KR) .................. 10-2019-0012024

(51) Int. Cl.
*C07C 69/604* (2006.01)

(52) U.S. Cl.
CPC .................. *C07C 69/604* (2013.01)

(58) Field of Classification Search
CPC ...... C07C 69/604; C07C 69/60; C07C 69/657; A61K 31/225; A61P 17/06; A61P 25/00
See application file for complete search history.

(56) References Cited

U.S. PATENT DOCUMENTS

| 9,532,968 B1 | 1/2017 | Nguyen |
| 2016/0237041 A1 | 8/2016 | Nguyen |
| 2016/0279092 A1 | 9/2016 | Chaudhuri et al. |

FOREIGN PATENT DOCUMENTS

| KR | 10-2017-0115044 A | 10/2017 |
| WO | WO-2015/043688 A1 | 4/2015 |
| WO | WO-2016/061393 A1 | 4/2016 |
| WO | WO-2016/124960 A1 | 8/2016 |

OTHER PUBLICATIONS

International Search Report from corresponding PCT Application No. PCT/KR2020/001368, dated May 20, 2020.
(Continued)

*Primary Examiner* — Deborah D Carr
(74) *Attorney, Agent, or Firm* — Harness, Dickey & Pierce, P.L.C.

(57) ABSTRACT

The present invention provides: novel compounds capable of producing monomethyl fumarate after the compounds are administered; pharmaceutical compositions comprising same as active ingredients; and pharmaceutical uses thereof for treating or alleviating various diseases including immune system abnormalities, neurodegeneration, and/or inflammatory diseases.

6 Claims, 3 Drawing Sheets

(56) References Cited

OTHER PUBLICATIONS

Albrecht, P., et al.; "Effects of dimethyl fumarate on neuroprotection and immunomodulation", Journal of Neuroinflammation 2012, 9:163.

Akkafa, F., et al.; "Reduced SIRT1 expression correlates with enhanced oxidative stress in compensated and decompensated heart failure", RedoxBiology6(2015) 169-173.

Gill, A. J., et al.; "Dimethyl fumarate modulation of immune and antioxidant responses: application to HIV therapy", Crit Rev Immunol. 2013 ; 33(4): 307-359.

Cross, S. A., et al.; "Dimethyl Fumarate, an Immune Modulator and Inducer of the Antioxidant Response, Suppresses HIV Replication and Macrophage-Mediated Neurotoxicity: A Novel Candidate for HIV Neuroprotection", The Journal of Immunology, 2011, 187: 5015-5025.

Zheng et al. New Approaches to Treating Alzheimer's Disease. Perspectives in Medicinal Chemistry 2015:7 1-8 doi: 10.4137/PMC.S13210.

Balak, D., et al.; "Fumaric acid esters in the management of psoriasis" Psoriasis: Targets and Therapy 2015:5 9-23.

U.Mrowietz, "Treatment of severe psoriasis with fumaric acid esters: scientific background and guidelines for therapeutic use", British Journal of Dermatology 1999; 141: 424±429.

Linker, R. A., ett al.; "Fumaric acid esters exert neuroprotective effects in neuroinflammation via activation of the Nrf2 antioxidant pathway", Brain 2011: 134; 678-692.

Hayashi, G., et al.; "Dimethyl fumarate mediates Nrf2-dependent mitochondrial biogenesis in mice and humans", Human Molecular Genetics, 2017, vol. 26, No. 15 2864-2873.

McBean, G. J., et al.; "Redox-based therapeutics in neurodegenerative disease", British Journal of Pharmacology (2017) 174 1750-1770.

Dimethyl Fumarate for Obstructive Sleep Apnea, Identifier: NCT02438137, May 31, 2017, pp. 1-10.

Assessment of Tecfidera@ in Radiologically Isolated Syndrome (RIS) (ARISE), Identifier: NCT02739542, Apr. 15, 2016, pp. 1-9.

Dimethyl Fumarate (DMF) in Systemic Sclerosis-Associated Pulmonary Arterial Hypertension, Identifier: NCT02981082, Dec. 2, 2016, pp. 1-7.

Cho, H., et al.; "Monomethyl fumarate promotes Nrf2- dependent neuroprotection in retinal ischemia-reperfusion", Journal of Neuroinflammation (2015) 12:239.

Booth, L., et al.; "Repurposing Tecfidera for cancer", Aging, Jul. 2016, vol. 8 No 7, pp. 1289-1290.

Toyama, T., et al.; "Therapeutic targeting of TAZ and YAP by dimethyl fumarate in systemic sclerosis fibrosis", J Invest Dermatol. Jan. 2018 ; 138(1): 78-88.

Grzegorzewska, A. P et al. Dimethyl Fumarate ameliorates pulmonary arterial hypertension and lung fibrosis by targeting multiple pathways. *Sci. Rep.* 7, 41605.

Kavian, N., et al.,; "The Nrf2-Antioxidant Response Element Signaling Pathway Controls Fibrosis and Autoimmunity in Scleroderma." Front. Immunol. 9:1896, pp. 1-14.

Puebla, A., et al.; "Blood Eosinophils, Fraction of Exhaled Nitric Oxide, and Serum Eosinophil Cationic Protein as Surrogate Markers for Sputum Eosinophils in Asthma: Influence of Treatment With Inhaled Corticosteroids", J Investig Allergol Clin Immunol 2018; vol. 28(3): 210-212.

Hong-yan Zhu et al., "4-Hydroxybenzyl alcohol derivatives and their sedative-hypnotic activities", RSC Adv., 2018, 8, pp. 19539-19550.

Office Action from corresponding Korean Patent Application No. 10-2019-0012024, dated Jan. 8, 2024.

MONOMETHYL FUMARATE PRECURSOR DRUG COMPOUNDS AND PHARMACEUTICAL COMPOSITIONS THEREOF

CROSS-REFERENCE TO RELATED APPLICATIONS

This application is a national phase application of PCT Application No. PCT/KR2020/001368, filed on Jan. 29, 2020, which claims the benefit and priority to Korean Patent Application No. 10-2019-0012024, filed on Jan. 30, 2019. The entire disclosures of the applications identified in this paragraph are incorporated herein by references.

TECHNICAL FIELD

The present invention relates to a novel prodrug of monomethyl fumarate known to be useful for the treatment or improvement of various diseases such as psoriasis, multiple sclerosis, atopy, asthma, arthritis, inflammatory bowel disease, lupus, amyotrophic lateral sclerosis, Huntington's disease, Alzheimer's disease, Parkinson's disease, macular degeneration, sleep apnea, radiologically isolated syndrome, scleroderma, cancer or tumor. The present invention also relates to a pharmaceutical composition comprising such a novel prodrug as an active ingredient. The present invention also relates to medical uses of such prodrug.

BACKGROUND ART

Dimethyl fumarate (DMF) is a methyl ester compound of fumaric acid. It is an active ingredient of Fumaderm (tablet), which is marketed as a treatment for psoriasis, and Tecfidera (capsule), which is commercially available as a treatment for multiple sclerosis. These products are pharmaceuticals for oral administration, and dimethyl fumarate is rapidly metabolized to monomethyl fumarate (MMF) after oral administration and exposed to the blood. The substance that actually shows medicinal effect is known as monomethyl fumarate. That is, dimethyl fumarate can be said to be a prodrug of the active metabolite monomethyl fumarate.

The physiological mechanism of action of monomethyl fumarate has been studied in various aspects so far, and several research results have been reported to identify the immunomodulatory function, antioxidant effect, nerve cell protection, and anti-inflammatory effect. (Journal of Neuroinflammation, 2012, 9, 163; Redox Biology, 2015, 169; Critical Reviews in Immunology, 2013, 33(4), 307; Journal of Immunology, 2011, 187(10), 5015; Perspectives in Medicinal Chemistry, 2015, 7, 1; Psoriasis: Targets and Therapy, 2015, 5, 9) Fumaderm that have already been commercialized comprises 4 fumaric acid esters (FAEs), dimethyl fumarate, ethyl hydrogen fumarate calcium salt, ethyl hydrogen fumarate magnesium salt, and ethyl hydrogen zinc salt. This drug was confirmed to be effective in patients with severe psoriasis, and the mechanism was reported to be related to selective immunomodulation (induction of Th2-selective cytokine secretion). (British Journal of Dermatology, 1999, 141, 424.)

In the case of Tecfidera containing dimethyl fumarate as an active ingredient, monomethyl fumarate, an active metabolite, has been reported to be effective for the treatment of multiple sclerosis diseases through activation of the Nrf2 (Nuclear factor (erythroid-derived 2)-like 2) pathway. (Brain, 2011, 678; Human Molecular Genetics, 2017, 26(15), 2864.) In addition, antioxidant Nrf2 activators such as monomethyl fumarate have been shown to be effective against various neurodegenerative diseases such as multiple sclerosis, Alzheimer's disease, Huntington's disease, Parkinson's disease, and amyotrophic lateral sclerosis. (British Journal of Pharmacology, 2017, 174(12), 1750.) In addition to the above diseases, monomethyl fumarate or dimethyl fumarate is known to be useful in the treatment, improvement or prevention of atopic dermatitis, macular degeneration, sleep apnea, radiologically isolated syndrome related to multiple sclerosis, scleroderma, systemic sclerosis-associated pulmonary arterial hypertension, cancer or tumor, etc. (https://clinicaltrials.gov/ct2/show/NCT02438137, https://clinicaltrials.gov/ct2/show/NCT02739542, https://clinicaltrials.gov/ct2/show/NCT02981082, J Neuroinflammation. 2015; 12: 239, Aging (Albany NY). 2016 July; 8(7): 1289-1290, J Invest Dermatol. 2018 January; 138(1):78-88, Nature Scientific Reports 7, Article number: 41605 (2017), Front Immunol. 2018; 9: 1896, J Investig Allergol Clin Immunol 2018; Vol. 28(3): 182-215).

Even though the above-mentioned psoriasis, multiple sclerosis, and inflammatory or neurodegenerative diseases are all intractable diseases that are very difficult or impossible to treat, products with already commercialized dimethyl fumarate as an active ingredient are recognized for its excellent clinical utility in the treatment of some diseases such as psoriasis and multiple sclerosis. However, due to the nature of the diseases, dimethyl fumarate preparations are known to be unavoidably taken for a long period of at least one month and have severe side effects.

For example, Tecfidera used as a treatment for multiple sclerosis has been commercialized in capsule form (120 mg and 240 mg). Its starting dose is 120 mg twice a day for 7 days, and then the recommended dose is to increase the dose to be 240 mg twice a day. However, side effects following long-term administration, such as gastrointestinal disorders (diarrhea, nausea, abdominal pain, epigastric pain), hot flush (flushing), lymphopenia, progressive multifocal leukoencephalopathy, etc., are common. It is known that gastrointestinal disorders are very common side effects that occur in 10-15% of patients and flushing occurs in 40% of patients. In addition, Tecfidera has a high risk of side effects above, so it is recommended to take it with food to improve tolerability. If flushing or gastrointestinal disorders are severe, the dose can be temporarily reduced to 120 mg twice a day. However, even in this case, the dose must be increased to 240 mg twice a day within 1 month.

As for prodrug of monomethyl fumarate, in addition to the existing dimethyl fumarate, several candidates with new chemical structures are in the clinical trial stage. For example, ALKS8700 (Alkemes, USA) is a diroximel fumarate compound, which is currently undergoing phase 3 clinical trial. This technology has been transferred to Biogen. (U.S. Pat. No. 8,669,281) In addition, XP23829 (Xenoport, USA) has completed phase 2 clinical trial, and this technology has been transferred to Dr. Reddy's Laboratories in India. (U.S. Pat. No. 8,148,414) These candidates are all prodrugs of monomethyl fumarate for development as a treatment for multiple sclerosis, focusing on improving the serious side effects of dimethyl fumarate, especially flushing and gastrointestinal disorders. The above two candidates has been proven to be safe in the phase 1 clinical trial. In terms of efficacy for the treatment of multiple sclerosis, when using the existing drug dimethyl fumarate as a reference drug, the characteristics of bioequivalent therapy compared to toxicity have not yet been sufficiently proven. In particular, in the case of the XP23829 candidate, the dosage administered in phase 2 clinical trial was 400 mg and 800 mg, respectively, once or twice a day in a capsule formulation, and the dosage was designed to be a higher compared to the existing dimethyl fumarate formulation.

SUMMARY

Technical Problem

Therefore, the problem to be solved by the present invention is to provide a monomethyl fumarate prodrug with reduced side effects and excellent pharmacokinetics, a pharmaceutical composition comprising such a drug, and medical uses of such a drug for treating or improving immune system abnormalities, neurodegenerative or inflammatory diseases.

Technical Solution

In order to solve the above problem, the present disclosure provides a compound represented by the following Chemical Formula 1.

[Chemical Formula 1]

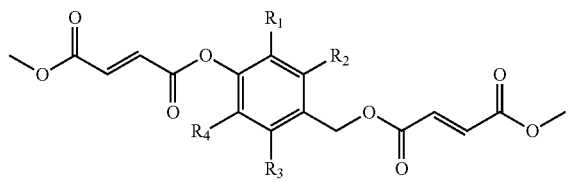

In the Chemical Formula 1,
$R_1$, $R_2$, $R_3$ and $R_4$ are each independently selected from the group consisting of hydrogen, —$(C_1$-$C_3)$alkyl, —$O(C_1$-$C_3)$alkyl, F, Cl, and Br.

As a result of preparing and evaluating various prodrugs, the present inventors completed the present invention by confirming that the compound exhibited very excellent effects in terms of improvement of side effects and pharmacokinetics, and exhibited excellent physical properties or characteristics as a prodrug in addition to these aspects.

In one embodiment of the present invention, preferably, the compound is
4-((E)-4-methoxy-4-oxobu-2-tenoyloxy)benzyl methyl fumarate;
2-methoxy-4-(((E)-4-methoxy-4-oxobu-2-tenoyloxy) methyl)phenyl methyl fumarate;
4-((E)-4-methoxy-4-oxobu-2-tenoyloxy)-2-methylbenzyl methyl fumarate;
3,5-difluoro-4-(((E)-4-methoxy-4-oxobu-2-tenoyloxy) methyl)phenyl methyl fumarate;
3-fluoro-4-(((E)-4-methoxy-4-oxobu-2-tenoyloxy)methyl) phenyl methyl fumarate;
or
3-chloro-4-(((E)-4-methoxy-4-oxobu-2-tenoyloxy)methyl) phenyl methyl fumarate.

As used herein, "Cx-Cy" means that the number of carbon atoms is x to y. For example, $(C_1$-$C_3)$alkyl means alkyl having 1 to 3 carbon atoms.

As used herein, the term "alkyl" includes both linear and branched forms, so in the case of $C_3$ alkyl, it may be isopropyl or normal propyl.

As used herein, the phrase "compound(s) of this/the invention" includes any compound(s) of Chemical Formula 1, as well as clathrates, hydrates, solvates, or polymorphs thereof.

As used herein, the term "polymorph" refers to solid crystalline forms of a compound of this disclosure or complex thereof. Different polymorphs of the same compound can exhibit different physical, chemical and/or spectroscopic properties. Different physical properties include, but are not limited to stability (e.g., to heat or light), compressibility and density (important in formulation and product manufacturing), and dissolution rates (which can affect bioavailability). Differences in stability can result from changes in chemical reactivity (e.g., differential oxidation, such that a dosage form discolors more rapidly when comprised of one polymorph than when comprised of another polymorph) or mechanical characteristics (e.g., tablets crumble on storage as a kinetically favored polymorph converts to thermodynamically more stable polymorph) or both (e.g., tablets of one polymorph are more susceptible to breakdown at high humidity). Different physical properties of polymorphs can affect their processing. For example, one polymorph might be more likely to form solvates or might be more difficult to filter or wash free of impurities than another due to, for example, the shape or size distribution of particles of it.

As used herein, the term "solvate" means a compound or its salt according to this disclosure that further includes a stoichiometric or non-stoichiometric amount of a solvent bound by non-covalent intermolecular forces. Preferred solvents are volatile, non-toxic, and acceptable for administration to humans in trace amounts.

As used herein, the term "hydrate" means a compound or its salt according to this disclosure that further includes a stoichiometric or non-stoichiometric amount of water bound by non-covalent intermolecular forces.

As used herein, the term "clathrate" means a compound or its salt in the form of a crystal lattice that contains spaces (e.g., channels) that have a guest molecule (e.g., a solvent or water) trapped within.

The compound represented by Chemical Formula 1 of the present invention may be synthesized, for example, by the following scheme.

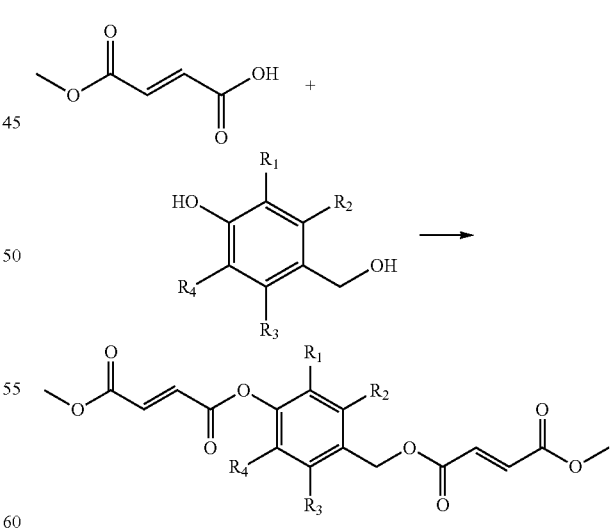

In the above scheme, $R_1$, $R_2$, $R_3$ and $R_4$ are the same as described above.

The compound represented by Chemical Formula 1 of the present invention can be obtained by ester condensation reaction of monomethyl fumarate with a 4-hydroxybenzyl alcohol derivative having substituents $R_1$, $R_2$, $R_3$ and $R_4$. In this reaction, monomethyl fumarate is used twice the equivalent of 4-hydroxybenzyl alcohol derivative. An activator can be chosen among various activators commonly used for esterification, such as N,N'-dicyclohexylcarbodiimide (DCC), 1-ethyl-3-(3-dimethylaminopropyl)carbodiimide (EDC) or its hydrochloride (EDC HCl), N,N'-diisopropylcarbodiimide (DIPC). The most preferred is 1-ethyl-3-(3-dimethylaminopropyl)carbodiimide hydrochloride. In addition, in order to increase the reaction rate, 4-dimethylaminopyridine (DMAP) may be added in a catalytic amount to 2 times equivalent if necessary. The reaction solvent may be selected from dimethylformamide (DMF), dimethyl sulfoxide (DMSO), tetrahydrofuran (THF), dichloromethane (MC), dichloroethane (DCE), and N-methylpyrrolidine (NMP), of which the most preferred is tetrahydrofuran. The reaction may be carried out at room temperature, and the reaction may be completed by stirring for 1 hour to 24 hours depending on the type of reactant. In addition, depending on the type of derivative, if necessary, it may be purified by extraction, chromatography, and recrystallization. All derivatives obtained according to the above method, that is, the compound represented by Chemical Formula 1, were all identified as white solids.

The present inventors modified the chemical structure of monomethyl fumarate to create a novel structure compound having sufficient oral absorption rate, desirable blood pharmacokinetics, desirable physicochemical properties and so on. After oral administration of the novel compound, the concentration of the monomethyl fumarate exposed to the blood is directly proportional to the efficacy of the drug for the treatment or improvement of various diseases such as various immune system abnormalities, neurodegenerative and/or inflammatory diseases. It means that the doses of intravenous and oral administration can be proportionally applied by comparing the concentration of the monomethyl fumarate exposed to the blood through the metabolic process after oral administration of the novel compound according to the present invention, based on the concentration of the monomethyl fumarate exposed in the blood after intravenous administration of monomethyl fumarate.

The present inventors prepared and evaluated compounds having various chemical structures in order to derive the above-mentioned novel compounds. In addition, considering that absorption of the drug is basically made by passive diffusion, it was evaluated whether it exhibits a certain degree of fat solubility. It also was evaluated whether it can show minimum solubility in order to prevent a decrease in absorption due to excessively low water solubility. In particular, by adopting as a linker derivatives of 4-hydroxybenzyl alcohol, which have been reported to have neuroprotective action and anti-inflammatory action (RSC Adv., 2018, 8, 19539), it is possible to increase the safety after metabolism in the body, and secure desirable pharmacokinetics as confirmed in the present invention. That is, the derivative of the present invention activates the pharmacological action of monomethyl fumarate and can be expected to reduce side effects. Linkers according to the present invention are preferred for several purposes of the present invention over other linkers of similar structure, for example —O-phenyl-O—, —O—CH$_3$-phenyl-CH$_3$—O— and the like.

Specifically, the pharmacokinetic evaluation result of the compound of Example 1 among the compounds of Chemical Formula 1 according to the present invention is, for example, the relative absorption of the orally administered compound of Example 1 compared to the orally administered control material, that is, dimethyl fumarate was 121.5%, and the relative absorption of the compound of Example 4 was 150.0%. In addition, the relative absorbance of another control material, that is, the compound of Reference Example 1 (XP23829) was 77.0%. Therefore, when the novel compound presented in the present invention was orally administered at the same molar ratio (mmol/kg) as the control material, the concentration of monomethyl fumarate exposed in the blood compared to the control material was very high, which means that the same medicinal effect can be exhibited by administration of a low dose.

In another embodiment, the present invention provides a pharmaceutical composition comprising the compound of Chemical Formula 1 according to the present invention and a pharmaceutically acceptable carrier.

As used herein, the term "effective amount" refers to an amount of a compound of the present invention sufficient to slow or minimize immune system abnormalities, neurodegenerative and/or inflammatory diseases; or an amount of a compound of the present invention sufficient to provide a therapeutic benefit in the treatment or management of immune system abnormalities, neurodegenerative and/or inflammatory diseases.

As the pharmaceutically acceptable carrier, for example, a carrier for oral administration or a carrier for parenteral administration may be used. Carriers for oral administration may include lactose, starch, cellulose derivatives, magnesium stearate, stearic acid, and the like. In addition, carriers for parenteral administration may include water, suitable oil, saline, aqueous glucose and glycol, and the like, and may further include stabilizers and preservatives. Suitable stabilizers may be antioxidants such as sodium hydrogen sulfite, sodium sulfite or ascorbic acid. Suitable preservatives may be benzalkonium chloride, methyl- or propyl-paraben and chlorobutanol. Other pharmaceutically acceptable carriers well known to those skilled in the art may be used.

The pharmaceutical composition of the present invention can be administered to mammals including humans by any route of administration. It can be administered orally or parenterally. However, the oral administration route is more preferable in view of the excellent oral absorption of the compounds of the present invention.

Parenteral administration methods include, for example, but are not limited thereto, intravenous, intramuscular, intraarterial, intramedullary, intrathecal, intracardiac, transdermal, subcutaneous, intraperitoneal, intranasal, intestinal, topical, sublingual or rectal administration. For example, the pharmaceutical composition of the present invention may be prepared in an injectable formulation and administered by a method of lightly pricking the skin with a 30 gauge thin injection needle, or directly applying it to the skin.

The pharmaceutical composition of the present invention may be formulated as a formulation for oral administration or parenteral administration according to the route of administration as described above.

In the case of a formulation for oral administration, the composition of the present invention may be formulated using a method known in the art such as powder, granule, tablet, pill, dragee, capsule, liquid, gel, syrup, slurry, suspension, etc. For example, oral preparations can be obtained as a tablet by blending the active ingredient with a solid excipient, pulverizing it, adding a suitable adjuvant, and processing it into a granule mixture. Examples of suitable excipients include diluents such as sugars including as lactose, dextrose, sucrose, sorbitol, mannitol, xylitol, erythritol and maltitol; starches including corn starch, wheat starch, rice starch and potato starch; celluloses including cellulose, methyl cellulose, sodium carboxymethylcellulose and hydroxypropylmethyl-cellulose; gelatin; polyvinylpyrrolidone; and the like. In addition, in some cases, cross-linked polyvinylpyrrolidone, agar, alginic acid or sodium alginate may be added as a disintegrant. Furthermore, the pharmaceutical composition of the present invention may further comprise an anti-aggregating agent, a lubricant, a wetting agent, a flavoring agent, an emulsifying agent and a preservative. In addition, in order to alleviate gastrointestinal irritation, the drug may be enteric-coated or microencapsulated in order to be released when passing through the intestinal tract rather than being released in the stomach.

In the case of a formulation for parenteral administration, it can be formulated in the form of injections, creams, lotions, ointments for external use, oils, moisturizers, gels, aerosols, and nasal inhalants by a method known in the art.

The total dosage of the pharmaceutical composition of the present invention may be administered to a patient as a single dose, and may be administered by a fractionated treatment protocol that is administered for a long time in multiple doses. The pharmaceutical composition of the present invention may vary the content of the active ingredient according to the symptoms of the disease. Preferably, the preferred total dose of the composition of the present invention may be about 0.01 μg to 1,000 mg, most preferably 1 mg to 100 mg per 1 kg of the patient's body weight per day. However, the appropriate effective dosage of the pharmaceutical composition of the present invention can be determined by conventional knowledge in the art based on the route of administration and the number of treatments as well as various factors such as the patient's age, weight, health condition, sex, disease severity, diet, and excretion rate. The pharmaceutical composition according to the present invention is not particularly limited to any specific formulation, route of administration, and method of administration as long as it exhibits the effects of the present invention.

In addition, the pharmaceutical composition of the present invention may be administered as an individual therapeutic agent or administered in combination with other therapeutic agents. When administered in combination with other therapeutic agents, the composition of the present invention and the other therapeutic agent(s) may be administered simultaneously, individually or sequentially. At this time, the other therapeutic agent may be a substance already known to have an effect of treating or improving immune system abnormalities, neurodegenerative and/or inflammatory diseases. When the pharmaceutical composition of the present invention is administered in combination with another therapeutic agent, the composition of the present invention and the other therapeutic agent may be separately formulated into separate containers, or may be formulated in combination in the same formulation.

In order to administer the compound presented in the present invention to the human body, a representative pharmaceutical method is described in detail with an enteric-coated tablet as an example, as shown in Table 1 below. Compounds A and B presented below refer to substances presented as active ingredients for the treatment, improvement or prevention of immune system abnormalities, neurodegenerative and/or inflammatory diseases in the present invention.

TABLE 1

| (Unit: wt %) | | Composition 1 | Composition 2 |
|---|---|---|---|
| Tablet before coating (Uncoated tablet) | Active ingredient | Compound A 10 | Compound B 12 |
| | Mannitol | 55 | 48 |
| | Hydroxypropyl cellulose | 20 | 25 |
| | Sodium stearyl fumarate | 1 | 1 |

TABLE 1-continued

| (Unit: wt %) | | Composition 1 | Composition 2 |
|---|---|---|---|
| Separating layer | Polyvinyl pyrrolidone | 2 | 2 |
| Enteric coating | Hypromellose phthalate | 10.3 | 10.3 |
| | Dibutyl sebacate | 1.2 | 1.2 |
| | Titanium dioxide | 0.5 | 0.5 |

The present invention also provides a pharmaceutical composition comprising a compound of Chemical Formula 1 according to the present invention as an active ingredient for the treatment or improvement of psoriasis, atopic dermatitis, macular degeneration, multiple sclerosis, asthma, arthritis, inflammatory bowel disease, lupus, amyotrophic lateral sclerosis, Huntington's disease, Alzheimer's disease, Parkinson's disease, sleep apnea, radiologically isolated syndrome, scleroderma, cancer or tumor. That is, the present invention provides a medical use of the compound of Chemical Formula 1 according to the present invention for treatment or improvement of the disease mentioned above.

In another aspect of the present invention, the present invention is to provide a method for treating or preventing psoriasis, atopic dermatitis, macular degeneration, multiple sclerosis, asthma, arthritis, inflammatory bowel disease, lupus, amyotrophic lateral sclerosis, Huntington's disease, Alzheimer's disease, Parkinson's disease, sleep apnea, radiologically isolated syndrome, scleroderma, cancer or tumor, comprising administering to a subject in need thereof a therapeutically effective amount of the compound of Chemical Formula 1. In another embodiment, the subject is a human. In one embodiment, the treatment is a preventative treatment. In another embodiment, the treatment is a palliative treatment. In another embodiment, the treatment is a restorative treatment.

Advantageous Effects

The present invention provides compounds effective for the treatment or improvement of various diseases such as immune system abnormalities, neurodegenerative or inflammatory diseases, pharmaceutical compositions comprising the compound(s) as an active ingredient, their medical uses, and treatment methods comprising administering the compound(s) to an individual in need of treatment or prevention. The compound according to the present invention is an active ingredient of a medicine, and has various advantages in terms of solubility and the like, and is particularly excellent in bioavailability and pharmacokinetics after oral administration.

BRIEF DESCRIPTION OF THE DRAWINGS

In FIG. 1, ▲ is the result of the oral administration group of dimethyl fumarate, and Δ is the result of the oral administration group of Example 1 compound.

2, ▲ is the result of the oral administration group of dimethyl fumarate, and Δ is the result of the oral administration group of Example 4 compound.

Figure 3:
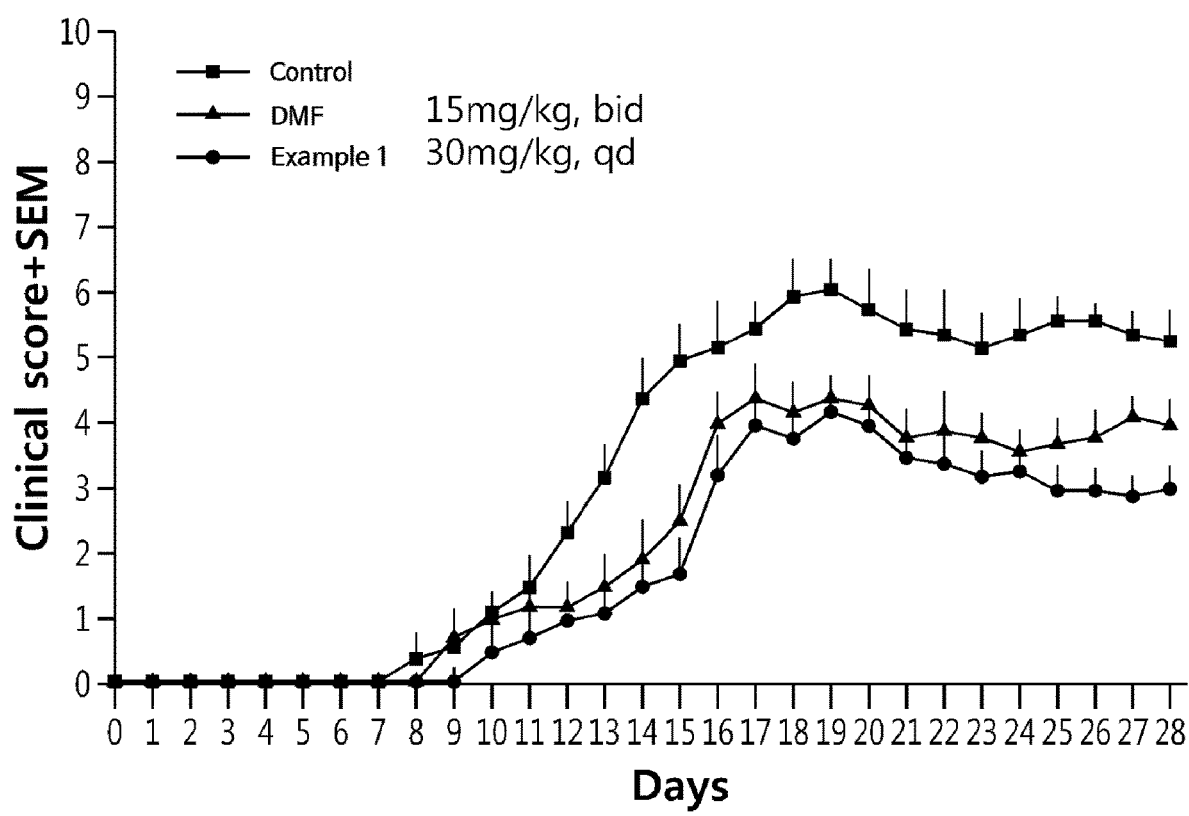

FIG. 3 is the efficacy results of a group administered with dimethyl fumarate twice a day (bid); a vehicle control group administered once a day (qd); and a group administered with the compound of Example 1 of the present invention once a day (qd) in a multiple sclerosis disease model using experimental autoimmune encephalomyelitis mice (EAE mice).

DETAILED DESCRIPTION

Hereinafter, the present invention will be described in more detail based on the following examples, which are not intended to limit the scope of the present invention. In addition, those of ordinary skill in the art will be able to make various changes and modifications to the present invention within a range that does not impair the spirit of the present invention.

First, examples of the compound of Chemical Formula 1 according to the present invention are described below. Representative examples along with specific preparation steps are described below, and compounds having different substituents may be prepared through similar steps. Those of ordinary skill in the art will be able to easily prepare compounds of Chemical Formula 1 with different substituents with reference to the following representative examples.

Reference Example 1: 2-(diethylamino)-2-oxoethyl Methyl Fumarate (XP23829)

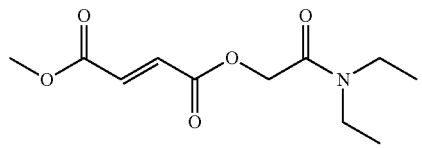

1.0 g of monomethyl fumarate was dissolved in 5 ml of dimethylformamide, and 1.0 g (0.67 equivalent) of 2-bromo-N,N-diethylacetamide and 2.01 g (0.8 equivalent) of cesium carbonate were added thereto. After stirring at room temperature for 1 hour, the mixture was filtered through celite, and then diluted with 80 ml of ethyl acetate. After washing 3 times with 80 ml of water, drying over anhydrous magnesium sulfate, concentration and crystallization with n-hexane, 0.5 g of a white solid was obtained. (Yield: 27%)
$^1$H NMR (400 MHz, CDCl$_3$) δ 1.13 (t, 3H), 1.23 (t, 3H), 3.25 (q, 2H), 3.39 (q, 2H), 3.80 (s, 3H), 4.83 (s, 2H), 6.95 (s, 1H), 6.96 (s, 1H)

Example 1: 4-((E)-4-methoxy-4-oxobu-2-tenoyloxy) benzyl Methyl Fumarate

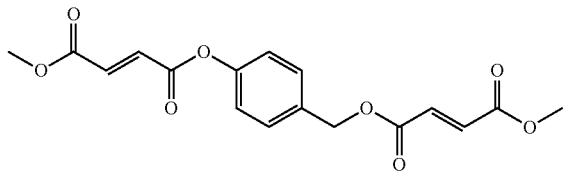

1.0 g of monomethyl fumarate was suspended in 20 ml of tetrahydrofuran, and 0.48 g (0.5 eq.) of 4-hydroxybenzyl alcohol, 3.68 g (2.5 eq.) of 1-ethyl-3-(3-dimethylaminopropyl)carbodiimide hydrochloride) and 0.94 g (1.0 eq.) of 4-dimethylaminopyridine were added. After stirring at room temperature for 8 hours, the mixture was concentrated and diluted with 20 ml of dichloromethane. After washing with 20 ml of water, drying over anhydrous magnesium sulfate, concentration, and crystallization with a mixed solvent of ethyl acetate and n-hexane (1:2, v/v), 0.66 g of the title compound as a white solid was obtained. (Yield: 49%)
$^1$H NMR (400 MHz, DMSO-d$_6$) δ 3.71 (s, 3H), 3.75 (s, 3H), 5.22 (s, 2H), 6.80 (s, 2H), 6.95 (s, 2H), 7.21 (d, 2H), 7.46 (d, 2H)

Example 2: 2-methoxy-4-(((E)-4-methoxy-4-oxobu-2-tenoyloxy)methyl)phenyl Methyl Fumarate

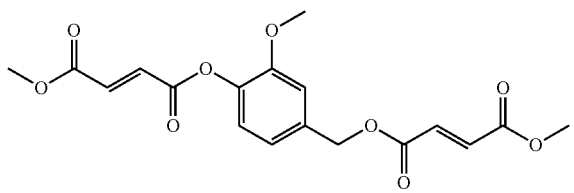

1.0 g of monomethyl fumarate was suspended in 20 ml of tetrahydrofuran, and 0.59 g (0.5 eq.) of 4-(hydroxymethyl)-2-methoxyphenol, 3.68 g (2.5 eq.) of 1-ethyl-3-(3-dimethylaminopropyl)carbodiimide hydrochloride and 0.94 g (1.0 eq.) of 4-dimethylaminopyridine were added. After stirring at room temperature for 24 hours, the mixture was concentrated and diluted with 20 ml of ethyl acetate. After washing with 20 ml of water, drying over anhydrous magnesium sulfate, concentration, and crystallization with a mixed solvent of ethyl acetate and n-hexane (1:5, v/v), 0.96 g of the title compound as a white solid was obtained. (Yield: 66%)
$^1$H NMR (400 MHz, DMSO-d$_6$) δ 3.71 (s, 3H), 3.74 (s, 6H), 5.20 (s, 2H), 6.81 (s, 2H), 6.95 (s, 2H), 7.00 (d, 1H), 7.15 (d, 1H), 7.20 (s, 1H)

Example 3: 4-((E)-4-methoxy-4-oxobu-2-tenoyloxy)-2-methylbenzyl Methyl Fumarate

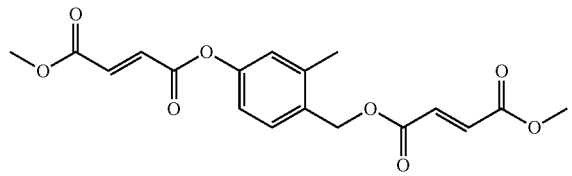

1.0 g of monomethyl fumarate was suspended in 20 ml of tetrahydrofuran, and 0.53 g (0.5 eq.) of 4-(hydroxymethyl)-3-methylphenol, 3.68 g (2.5 eq.) of 1-ethyl-3-(3-dimethylaminopropyl)carbodiimide hydrochloride and 0.94 g (1.0 eq.) of 4-dimethylaminopyridine were added. After stirring at room temperature for 24 hours, the mixture was concentrated and diluted with 20 ml of ethyl acetate. After washing with 20 ml of water, drying over anhydrous magnesium sulfate, and crystallization with a mixed solvent of ethyl acetate and n-hexane (1:5, v/v), 0.93 g of the title compound as a white solid was obtained. (Yield: 67%)

$^1$H NMR (400 MHz, DMSO-d$_6$) δ 2.29 (s, 3H), 3.70 (s, 3H), 3.75 (s, 3H), 5.22 (s, 2H), 6.79 (s, 2H), 6.94 (s, 2H), 7.03 (d, 1H), 7.08 (s, 1H), 7.40 (d, 1H)

Example 4: 3,5-difluoro-4-(((E)-4-methoxy-4-oxobut-2-tenoyloxy)methyl)phenyl Methyl Fumarate

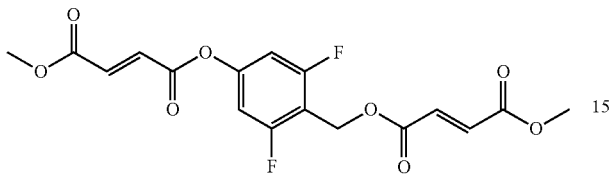

1.0 g of monomethyl fumarate was suspended in 20 ml of tetrahydrofuran, and 0.62 g (0.5 eq.) of 3,5-difluoro-4-(hydroxymethyl)phenol, 3.68 g (2.5 eq.) of 1-ethyl-3-(3-dimethylaminopropyl)carbodiimide hydrochloride and 0.94 g (1.0 eq.) of 4-dimethylaminopyridine were added. After stirring at room temperature for 4 hours, the mixture was concentrated and diluted with 20 ml of dichloromethane. After washing with 20 ml of water, drying over anhydrous magnesium sulfate, concentration, and purification by column chromatography using silica gel (a mixed solvent of ethyl acetate and n-hexane, 1:3, v/v), 0.74 g of the title compound as a white solid was obtained. did. (Yield: 50%)

$^1$H NMR (400 MHz, DMSO-d$_6$) δ 3.69 (s, 3H), 3.75 (s, 3H), 5.26 (s, 2H), 6.75 (s, 2H), 6.94 (s, 1H), 6.96 (s, 1H), 7.21 (s, 1H), 7.23 (s, 1H)

Example 5: 3-Fluoro-4-(((E)-4-methoxy-4-oxobu-2-tenoyloxy)methyl)phenyl Methyl Fumarate

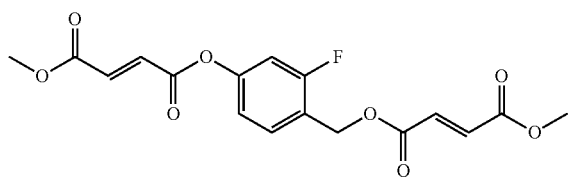

1.0 g of monomethyl fumarate was suspended in 20 ml of tetrahydrofuran, and 0.55 g (0.5 eq.) of 3-fluoro-4-(hydroxymethyl)phenol, 3.68 g (2.5 eq.) of 1-ethyl-3-(3-dimethylaminopropyl)carbodiimide hydrochloride and 0.94 g (1.0 eq.) of 4-dimethylaminopyridine were added. After stirring at room temperature for 8 hours, the mixture was concentrated and diluted with 20 ml of dichloromethane. After washing with 20 ml of water, drying over anhydrous magnesium sulfate, concentration, and purification by column chromatography using silica gel (a mixed solvent of ethyl acetate and n-hexane, 1:3, v/v), 0.84 g of the title compound as a white solid was obtained. (Yield: 59%)

$^1$H NMR (400 MHz, DMSO-d$_6$) δ 3.75 (s, 3H), 3.79 (s, 3H), 5.26 (s, 2H), 6.78 (s, 2H), 6.95 (s, 2H), 7.12 (d, 1H), 7.28 (d, 1H), 7.58 (dd, 1H)

Example 6: 3-Chloro-4-(((E)-4-methoxy-4-oxobu-2-tenoyloxy)methyl)phenyl Methyl Fumarate

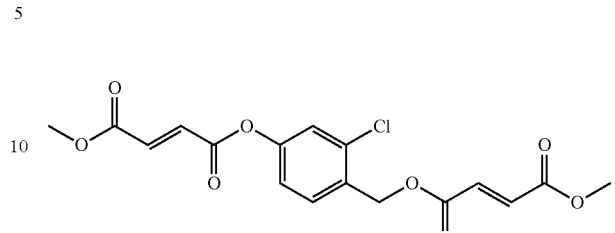

1.0 g of monomethyl fumarate was suspended in 20 ml of tetrahydrofuran, and 0.61 g (0.5 eq.) of 3-chloro-4-(hydroxymethyl)phenol, 3.68 g (2.5 eq.) of 1-ethyl-3-(3-dimethylaminopropyl)carbodiimide hydrochloride and 0.94 g (1.0 eq.) of 4-dimethylaminopyridine were added. After stirring at room temperature for 8 hours, the mixture was concentrated and diluted with 20 ml of dichloromethane. After washing with 20 ml of water, drying over anhydrous magnesium sulfate, concentration, and purification by column chromatography using silica gel (a mixed solvent of ethyl acetate and n-hexane, 1:2, v/v), 0.96 g of the title compound as a white solid was obtained. (Yield: 65%)

$^1$H NMR (400 MHz, DMSO-d$_6$) δ 3.71 (s, 3H), 3.75 (s, 3H), 5.28 (s, 2H), 6.81 (s, 2H), 6.95 (s, 2H), 7.25 (d, 1H), 7.49 (s, 1H), 7.62 (d, 1H)

Experimental Example 1: Pharmacokinetic Evaluation

Pharmacokinetic tests for the compounds of Examples and Reference Example were performed as follows. The test materials were each compound prepared in Examples 1 to 6, and the control materials were dimethyl fumarate (Sigma-Aldrich, catalog number 50744), which is the active ingredient of Tecfidera, and the compound prepared in Reference Example 1 (XP-23829). After a single oral administration of the six test compounds and two control compounds to SD (Sprague-Dawley) rats, the concentration of monomethyl fumarate released into the blood by the metabolic process over time was traced and analyzed, by which the efficacy of the compounds of the present invention was evaluated.

The test compounds and control compounds were each prepared in the same way and administered at a dose of 0.139 mmol/kg to rats, and after blood was collected at a predetermined time, plasma was separated. Analysis of the drug was performed using HPLC (XBridge column C$_{18}$, Waters, mobile phase 0.1% formic acid:acetonitrile (30:70, %/%)) and MS/MS (ESI positive, MRM). Each commercial standard solution was mixed with rat blank plasma at a ratio of 9:1 to prepare standard solutions and calibrate at concentrations of 5, 50, 100, 500, 100 and 5,000 ng/ml. In addition, the QC sample was prepared at 100, 750 and 2,500 ng/ml concentrations by mixing rat blank plasma and QC standard solution in a 9:1 ratio. As for the pretreatment method, 100 μl of the plasma sample was transferred to a centrifuge tube, and 10 μl of the internal standard solution and 300 μl of methanol were added and mixed for about 30 seconds. The tube was centrifuged at 3,000×g (4° C.) for about 5 minutes, and the supernatant was transferred to an LC vial and then injected into the instrument. And the concentration of the active ingredient in rat plasma, that is, monomethyl fumarate, was quantified by applying the previously verified assay. For pharmacokinetic parameters, WinNonlin 5.2 (Pharsight, USA) program was used, and $AUC_{0-t}$, $AUC_{0-\infty}$, $C_{max}$, $T_{max}$, and $t_{1/2}$ were calculated by noncompartment modeling (best fit). Pharmacokinetic parameter results were expressed as mean (Mean) and standard deviation (SD), and statistically processed using the SPSS program (Statistical Package for the Social Sciences, 10.0K, USA).

As a result of the test, the bioavailability after oral administration of the control compounds and the test compounds are summarized in Table 2 below.

TABLE 2

| | Sample | $AUC_{0-24}$ (ng/ml) | Standard Deviation (SD) | Relative absorption rate (Compared to dimethyl fumarate, %) | Route of administration |
|---|---|---|---|---|---|
| Control compound | Dimethyl fumarate | 10,746 | 3,028 | 100.0 | Oral |
| | Reference Example 1 (XP23829) | 8,278 | 668 | 77.0 | Oral |
| Test compound | Example 1 | 13,054 | 530 | 121.5 | Oral |
| | Example 2 | 14,550 | 882 | 135.4 | Oral |
| | Example 3 | 13,991 | 1,024 | 130.2 | Oral |
| | Example 4 | 16,117 | 3,977 | 150.0 | Oral |
| | Example 5 | 15,764 | 3,029 | 146.7 | Oral |
| | Example 6 | 15,592 | 2,245 | 145.1 | Oral |

Figure 1:
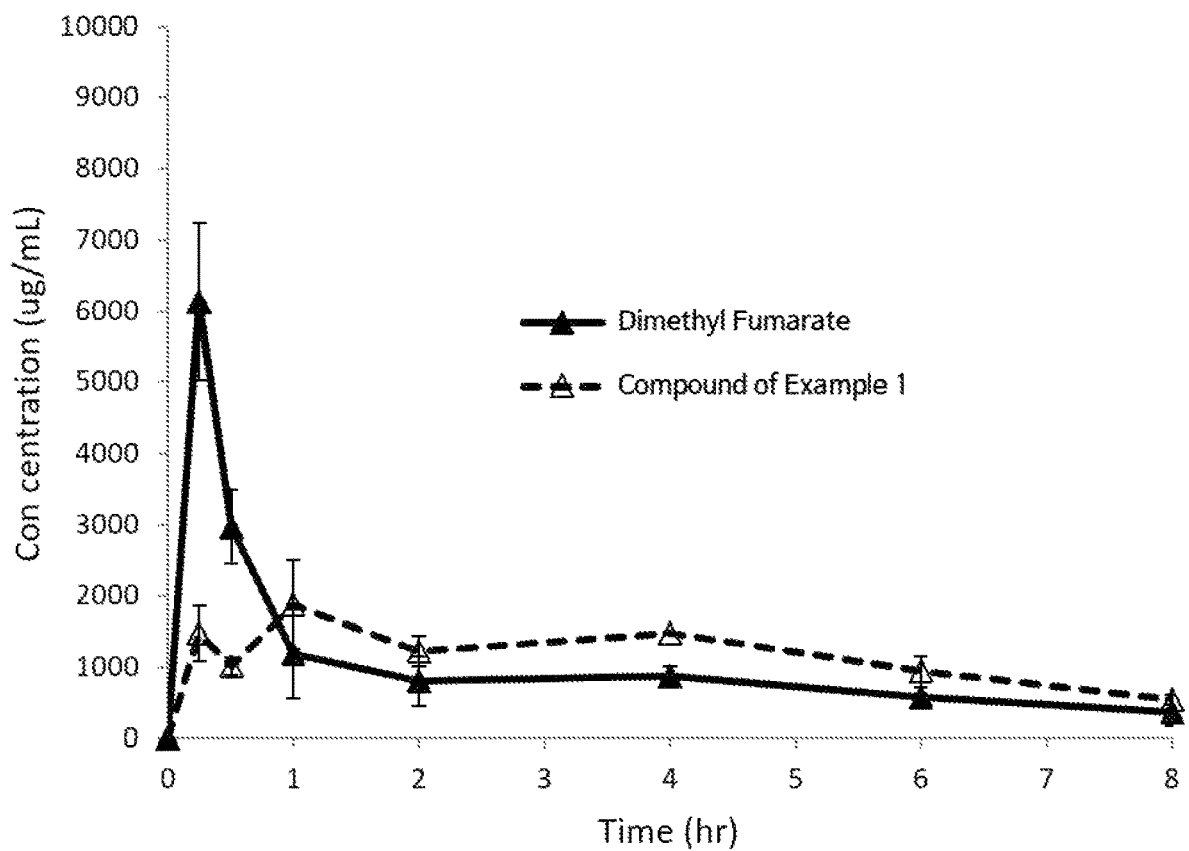
FIG. 1 is a graph showing the time-dependent blood concentration of monomethyl fumarate in rats after oral administration of a control material, dimethyl fumarate, and a single oral administration of the compound of Example 1, an embodiment according to the present invention.
Figure 2:
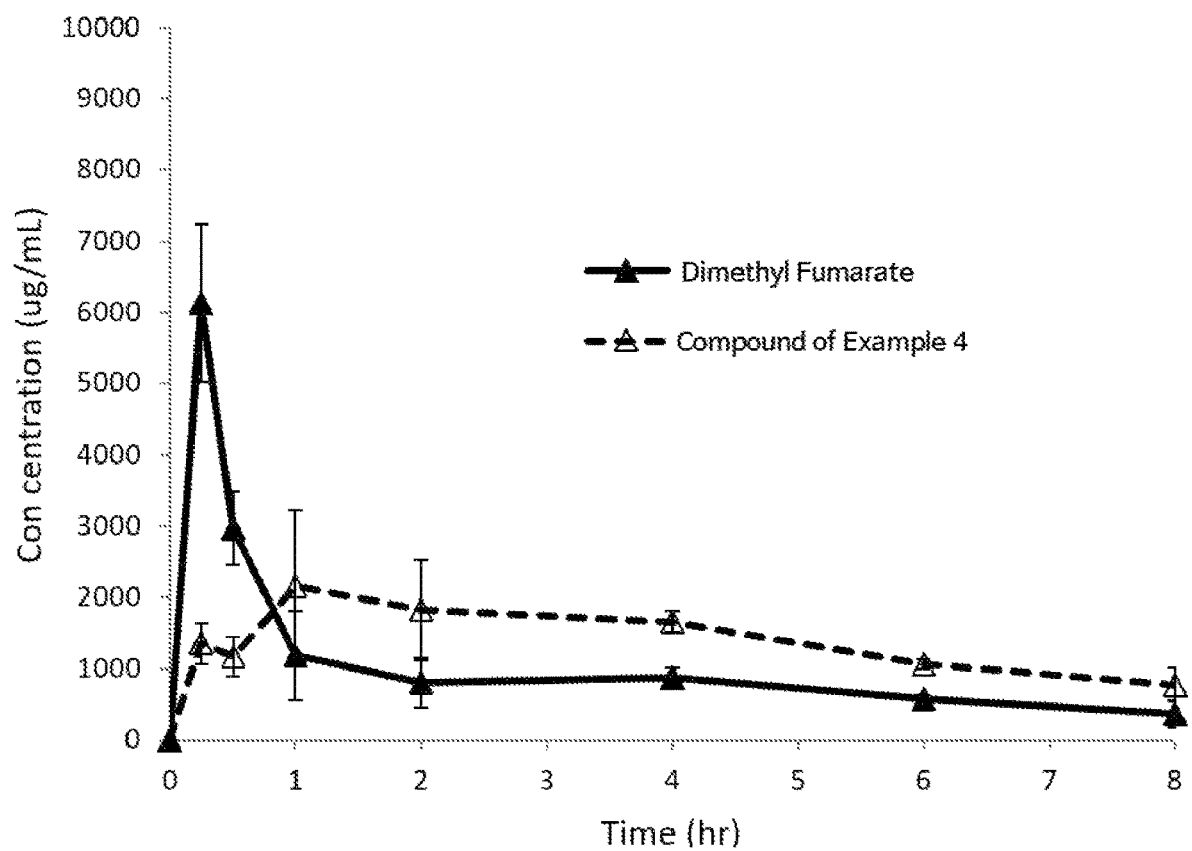
FIG. 2 is a graph showing the time-dependent blood concentration of monomethyl fumarate in rats after oral administration of a control material, dimethyl fumarate, and a single oral administration of the compound of Example 4, an embodiment according to the present invention. In FIG.

Representatively, for the compound of Example 1, the average $AUC_t$ is 13,054 hr*ng/ml, the average $AUC_i$ is 13,712 hr*ng/ml, the average $C_{max}$ is 1,916 ng/ml, the average $T_{max}$ is 2.50 hours, the average $t_{1/2}$ is 5.65 hours, and the relative absorption compared to dimethyl fumarate was 121.5%. On the other hand, in the case of the compound of Example 4, the average $AUC_t$ is 16,117 hr*ng/ml, the average $AUC_i$ is 16,629 hr*ng/ml, the average $C_{max}$ is 2,242 ng/ml, the average $T_{max}$ is 0.63 hours, the average $t_{1/2}$ is 4.82 hours, and the relative absorption compared to dimethyl fumarate was 150.0%. After oral administration of the compounds of Example 1 and Example 4, the trend of monomethyl fumarate blood concentration over time was compared with dimethyl fumarate, a control compound, as shown in FIGS. 1 (Table 3) and 2 (Table 4), respectively. As shown in the results of Table 2, the oral administration bioavailability of the Example compounds was excellent.

TABLE 3

| (μg/mL) | Compound of Example 1 | |
|---|---|---|
| time (h) | mean | SD |
| 0 | 0 | 0 |
| 0.25 | 1474 | 399 |
| 0.5 | 1009 | 127 |
| 1 | 1888 | 632 |
| 2 | 1227 | 220 |
| 4 | 1483 | 21 |

TABLE 3-continued

| (μg/mL) | Compound of Example 1 | |
|---|---|---|
| time (h) | mean | SD |
| 6 | 941 | 216 |
| 8 | 541 | 63 |
| 12 | 328 | 110 |
| 24 | 79 | 25 |
| $AUC_{0-24}$ | 13054 | 530 |
| $AUC_{inf}$ | 13712 | 835 |
| $C_{max}$ | 1916 | 591 |
| $T_{max}$ | 2.50 | 2.12 |
| $T_{1/2}$ | 5.65 | 0.82 |

TABLE 4

| (μg/mL) | Compound of Example 4 | |
|---|---|---|
| time (h) | mean | SD |
| 0 | 0 | 0 |
| 0.25 | 1356 | 291 |
| 0.5 | 1168 | 284 |
| 1 | 2164 | 1071 |
| 2 | 1825 | 703 |
| 4 | 1664 | 144 |
| 6 | 1063 | 77 |
| 8 | 772 | 237 |
| 12 | 462 | 293 |
| 24 | 72 | 17 |
| $AUC_{0-24}$ | 16117 | 3977 |
| $AUC_{inf}$ | 16629 | 3780 |
| $C_{max}$ | 2242 | 962 |
| $T_{max}$ | 0.63 | 0.53 |
| $T_{1/2}$ | 4.82 | 0.77 |

Experimental Example 2: Multiple Sclerosis Animal Model (EAE) Evaluation

The compound of Example 1 according to the present invention was evaluated for symptoms and efficacy using experimental autoimmune encephalomyelitis mice (EAE mice).

Specifically, for the EAE experiment, 8-12 week old female C57BL/6 mice (Central Lab. Animal Inc., South Korea) were used, and the average weight reached 20-30 g.

100 µg of myelin oligodendrocyte glycoprotein 35-55 (MOG) was prepared for EAE induction and was mixed with complete Freund's adjuvant (CFA; Difco, USA) containing 400 µg of *Mycobacterium tuberculosis* H37RA (Difco, USA). Then, 0.1 ml of the emulsion was subcutaneously injected into both waists of the EAE group, and 200 ng of pertussis toxin (PTX, List Biological Lab, USA) was injected intraperitoneally on day O and day 2, respectively.

The scale of clinical symptoms of EAE animal model induced by MOG peptide was evaluated in 10 steps according to Table 5 below along with daily body weight.

TABLE 5

| Grade | Clinical sign |
|---|---|
| 0 | No clinical signs |
| 1 | Normal gait, tip of the tail droops |
| 2 | Normal gait, tail droops |
| 3 | Hind limb paresis, uncoordinated movement |
| 4 | One hind limb paralyzed |
| 5 | Both hind limbs paralyzed |
| 6 | Hind limbs paralyzed, weakness in forelimbs |
| 7 | Hind limbs paralyzed, one forelimb paralyzed |
| 8 | Hind limbs paralyzed, both forelimbs paralyzed, mouse cannot move |
| 9 | Moribund, no movement, altered breathing |
| 10 | Death |

From Day 3, for the vehicle group (0.1% HPMC in sterile water, qd), the positive control group (dimethyl fumarate, DMF, 15 mg/kg, bid), and the test group (the compound of Example 1 30 mg/kg, qd), 10 animals in each group were orally administered through oral gavage after preparing a suspension using 0.1% HPMC in sterile water. The results of clinical scores for each administration group are shown in FIG. 3.

The compound of the present invention has a relatively high blood AUC for the active ingredient monomethyl fumarate compared to dimethyl fumarate, a control, in in vivo pharmacokinetic results, and, conversely, has a low $C_{max}$ and extended-release profile with an increased half-life. This suggests that the compound of the present can maintain the blood concentration of the active ingredient by administration once a day, in contrast to the pharmacokinetic properties of dimethyl fumarate that require administration twice a day.

On the other hand, the most common clinical side effects of dimethyl fumarate are gastrointestinal side effects and flushing, which are the two biggest reasons for discontinuing the drug. In general, side effects of a drug often occur due to a rapid increase in blood concentration of the drug, so it can be expected that the side effects will be reduced if it has the same blood concentration pattern as the compound of the present invention.

In addition, hot flushes are due to the pharmacological action of MMF, an active ingredient, and it is thought that it can be overcome clinically by having the characteristics of a sustained-release type that lowers $C_{max}$ and increases the half-life. Facial flushing, observed at a high rate when administering DMF clinically, appears over several months from the moment of DMF administration, and may be adapted or disappear after long-term administration, but the administration may be discontinued depending on the patient. The hot flush caused by DMF is very similar to the phenomenon that occurs when niacin is administered, and it is reported that Prostaglandin D2 (PGD2) is involved. In fact, according to the International Journal of Clinical Therapeutics/Volume 35, Number 10, 2013, it is reported that the plasma concentration of 9α,11β-PGF2 (9α,11β-prostaglandin F2), which is a major metabolite of PGD2, increases when DMF is administered. In the literature, it is reported that the concentration of 9α,11β-PGF2 in the blood decreases to a placebo level when Day 4 is reached when the sustained-release formulation of DMF is administered. However, DMF is not effective in reducing hot flashes because it has the pharmacokinetic properties of reducing 3 times a day administration to 2 times a day in the case of Tecfidera on the market, even if it is a sustained-release formulation. Thus, it is recommended that it is clinically used in combination with aspirin. Unlike DMF, which is a short-acting prodrug of MMF, the compound of the present invention has sustained-release properties of MMF, and excellent efficacy and reduced side effects are predicted when combined with sustained-release formulation technology in clinical practice.

The compounds of the present invention have a pharmacokinetic profile having sustained-release properties while maintaining a high blood concentration of MMF, and at the same time have excellent efficacy exceeding that of DMF administered twice a day with only once a day administration in an autoimmune disease model.

What is claimed is:

1. A compound represented by the following Chemical formula 1,

[Chemical Formula 1]

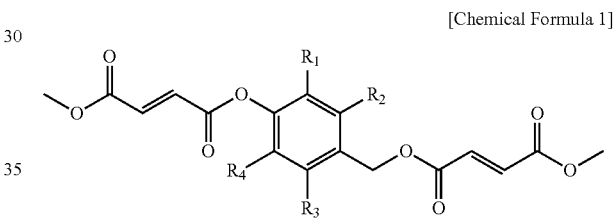

In Chemical Formula 1,
$R_1$, $R_2$, $R_3$ and $R_4$ are each independently selected from the group consisting of hydrogen, —(C1-C3)alkyl, —O—(C1-C3)alkyl, F, Cl, and Br.

2. The compound according to claim 1, wherein the compound is
4-((E)-4-methoxy-4-oxobu-2-tenoyloxy)benzyl methyl fumarate;
2-methoxy-4-(((E)-4-methoxy-4-oxobu-2-tenoyloxy) methyl)phenyl methyl fumarate;
4-((E)-4-methoxy-4-oxobu-2-tenoyloxy)-2-methylbenzyl methyl fumarate;
3,5-difluoro-4-(((E)-4-methoxy-4-oxobu-2-tenoyloxy) methyl)phenyl methyl fumarate;
3-fluoro-4-(((E)-4-methoxy-4-oxobu-2-tenoyloxy) methyl)phenyl methyl fumarate;
or
3-chloro-4-(((E)-4-methoxy-4-oxobu-2-tenoyloxy) methyl)phenyl methyl fumarate.

3. A pharmaceutical composition comprising the compound of claim 1 and a pharmaceutically acceptable carrier.

4. The pharmaceutical composition of claim 3, wherein the compound is
4-((E)-4-methoxy-4-oxobu-2-tenoyloxy)benzyl methyl fumarate;
2-methoxy-4-(((E)-4-methoxy-4-oxobu-2-tenoyloxy) methyl)phenyl methyl fumarate;
4-((E)-4-methoxy-4-oxobu-2-tenoyloxy)-2-methylbenzyl methyl fumarate;

3,5-difluoro-4-(((E)-4-methoxy-4-oxobu-2-tenoyloxy)
methyl)phenyl methyl fumarate;

3-fluoro-4-(((E)-4-methoxy-4-oxobu-2-tenoyloxy)
methyl)phenyl methyl fumarate;

or 3-chloro-4-(((E)-4-methoxy-4-oxobu-2-tenoyloxy)
methyl)phenyl methyl fumarate.

5. A method for treating or improving psoriasis, atopic dermatitis, macular degeneration, multiple sclerosis, asthma, arthritis, inflammatory bowel disease, lupus, amyotrophic lateral sclerosis, Huntington's disease, Alzheimer's disease, Parkinson's disease, sleep apnea, radiologically isolated syndrome, scleroderma, cancer, or tumor, the method comprising:

administering to a subject in need thereof a therapeutically effective amount of the compound of claim 1.

6. The method of claim 5, wherein the compound is 4-((E)-4-methoxy-4-oxobu-2-tenoyloxy)benzyl methyl fumarate;

2-methoxy-4-(((E)-4-methoxy-4-oxobu-2-tenoyloxy)
methyl)phenyl methyl fumarate;

4-((E)-4-methoxy-4-oxobu-2-tenoyloxy)-2-methylbenzyl methyl fumarate;

3,5-difluoro-4-(((E)-4-methoxy-4-oxobu-2-tenoyloxy)
methyl)phenyl methyl fumarate;

3-fluoro-4-(((E)-4-methoxy-4-oxobu-2-tenoyloxy)
methyl)phenyl methyl fumarate;

or 3-chloro-4-(((E)-4-methoxy-4-oxobu-2-tenoyloxy)
methyl)phenyl methyl fumarate.

\* \* \* \* \*